United States Patent
Xue et al.

(10) Patent No.: US 11,823,795 B2
(45) Date of Patent: Nov. 21, 2023

(54) CALLING DEVICE OF MAGNETIC RESONANCE IMAGING SYSTEM AND MAGNETIC RESONANCE IMAGING SYSTEM

(71) Applicant: Siemens Healthcare GmbH, Erlangen (DE)

(72) Inventors: Ting Qiang Xue, Shenzhen (CN); JianMin Wang, Shenzhen (CN); Jian Hong Liu, Shenzhen (CN)

(73) Assignee: Siemens Healthcare GmbH, Erlangen (DE)

( * ) Notice: Subject to any disclaimer, the term of this patent is extended or adjusted under 35 U.S.C. 154(b) by 0 days.

(21) Appl. No.: 17/534,605

(22) Filed: Nov. 24, 2021

(65) Prior Publication Data
US 2022/0165406 A1    May 26, 2022

(30) Foreign Application Priority Data
Nov. 24, 2020    (CN) .......................... 202011332790.5

(51) Int. Cl.
| | | |
|---|---|---|
| *G16H 40/60* | (2018.01) | |
| *H04W 4/30* | (2018.01) | |
| *G16H 40/63* | (2018.01) | |
| *G06K 7/10* | (2006.01) | |
| *G08B 5/22* | (2006.01) | |
| *G08B 3/10* | (2006.01) | |

(52) U.S. Cl.
CPC ......... *G16H 40/63* (2018.01); *G06K 7/10366* (2013.01); *H04W 4/30* (2018.02); *G08B 3/1041* (2013.01); *G08B 5/228* (2013.01)

(58) Field of Classification Search
CPC ..................................................... G16H 40/63
See application file for complete search history.

(56) References Cited

U.S. PATENT DOCUMENTS

| | | | | |
|---|---|---|---|---|
| 2010/0130140 A1* | 5/2010 | Waku | ..................... | H01Q 1/243 455/77 |
| 2010/0323650 A1* | 12/2010 | Egawa | ..................... | H04B 1/18 455/193.1 |
| 2011/0220470 A1* | 9/2011 | Diem | ................... | H01H 1/0036 200/181 |

(Continued)

*Primary Examiner* — Mohamed Barakat
*Assistant Examiner* — Pameshanand Mahase
(74) *Attorney, Agent, or Firm* — Banner & Witcoff Ltd.

(57) ABSTRACT

A calling device of a MRI system may include a reader/writer and a call maker. The reader/writer can send a fixed-frequency electromagnetic wave. The call maker may include a main body, an antenna, an operating member, and an answering controller. The antenna can generate an induced current after receiving the fixed-frequency electromagnetic wave. The operating member can switch between first and second positions relative to the main body. The answering controller is configured such that: when the operating member is in the first position, a first radio-frequency signal is sent through the antenna with energy obtained from the induced current generated by the antenna, and when the operating member is in the second position, a second radio-frequency signal is sent through the antenna with energy obtained from the induced current generated by the antenna. The reader/writer can send different prompt signals according to the first and second radio-frequency signals.

14 Claims, 4 Drawing Sheets

(56) References Cited

U.S. PATENT DOCUMENTS

| | | | |
|---|---|---|---|
| 2015/0380825 A1* | 12/2015 | Ryu | H01Q 9/16 |
| | | | 343/822 |
| 2017/0168481 A1* | 6/2017 | Flanigan | G05D 1/0022 |
| 2018/0233824 A1* | 8/2018 | Choi | H01Q 5/378 |
| 2019/0298899 A1* | 10/2019 | Hu | A61M 1/80 |
| 2022/0061776 A1* | 3/2022 | Souissi | A61B 5/746 |

* cited by examiner

CALLING DEVICE OF MAGNETIC RESONANCE IMAGING SYSTEM AND MAGNETIC RESONANCE IMAGING SYSTEM

CROSS REFERENCE TO RELATED APPLICATIONS

This patent application claims priority to Chinese Patent Application No. 202011332790.5, filed Nov. 24, 2020, which is incorporated herein by reference in its entirety.

BACKGROUND

Field

The present disclosure relates to a calling device, and in particular to a calling device for a magnetic resonance imaging system, and a magnetic resonance imaging system including the calling device.

Related Art

Magnetic resonance imaging (MRI) is a medical imaging technology that can be used for disease diagnosis. When an examinee is subjected to an examination in a detection area of a magnetic resonance imaging system, for bringing convenience to the examinee to send a call signal to an operator, the magnetic resonance imaging system is usually provided with a calling device. The existing calling device is substantially implemented by means of a squeezing ball, the squeezing ball is connected to an air hose, and the other end of the air hose is connected to an electronic pressure sensor. When the examinee presses the squeezing ball, the electronic pressure sensor generates an electric signal under the action of air pressure to trigger an alarm. The air hose is easily broken or mechanically squeezed during use, resulting in a failure of transmitting air pressure from the squeezing ball to the electronic pressure sensor, thereby causing a failure of triggering the alarm.

BRIEF DESCRIPTION OF THE DRAWINGS/FIGURES

The accompanying drawings, which are incorporated herein and form a part of the specification, illustrate the embodiments of the present disclosure and, together with the description, further serve to explain the principles of the embodiments and to enable a person skilled in the pertinent art to make and use the embodiments.

The exemplary embodiments of the present disclosure will be described with reference to the accompanying drawings. Elements, features and components that are identical, functionally identical and have the same effect are—insofar as is not stated otherwise—respectively provided with the same reference character.

DETAILED DESCRIPTION

In the following description, numerous specific details are set forth in order to provide a thorough understanding of the embodiments of the present disclosure. However, it will be apparent to those skilled in the art that the embodiments, including structures, systems, and methods, may be practiced without these specific details. The description and representation herein are the common means used by those experienced or skilled in the art to most effectively convey the substance of their work to others skilled in the art. In other instances, well-known methods, procedures, components, and circuitry have not been described in detail to avoid unnecessarily obscuring embodiments of the disclosure. The connections shown in the figures between functional units or other elements can also be implemented as indirect connections, wherein a connection can be wireless or wired. Functional units can be implemented as hardware, software or a combination of hardware and software.

An objective of the present disclosure is to provide a calling device of a magnetic resonance imaging system. The calling device has high reliability.

Another objective of the present disclosure is to provide a magnetic resonance imaging system, and a calling device of the magnetic resonance imaging system that has high reliability.

The present disclosure provides a calling device of a magnetic resonance imaging system. The calling device includes a reader/writer and a call maker. The reader/writer can send a fixed-frequency electromagnetic wave to form a radio-frequency electromagnetic field in a detection area of the magnetic resonance imaging system. The call maker includes a main body, an antenna, an operating member, and an answering controller. The antenna is arranged on the main body and can generate an induced current after receiving the foregoing fixed-frequency electromagnetic wave. The operating member is arranged on the main body and can switch between a first position and a second position relative to the main body. The answering controller is arranged on the main body and connected to the antenna. The answering controller is configured such that: when the operating member is in the first position, the answering controller can send a first radio-frequency signal through the antenna with energy obtained from the induced current generated by the antenna, and when the operating member is in the second position, the answering controller can send a second radio-frequency signal through the antenna with energy obtained from the induced current generated by the antenna. The reader/writer can receive the first radio-frequency signal and the second radio-frequency signal and can send different prompt signals according to the first radio-frequency signal and the second radio-frequency signal respectively.

In the calling device of the magnetic resonance imaging system, an RFID (Radio Frequency Identification) technology is used to realize wireless interconnection between the reader/writer and the call maker, helping an operator to make a determination in time to stop an examination when the calling device has a fault, and in this way, high reliability is achieved.

In another exemplary implementation of the calling device of a magnetic resonance imaging system, the answering controller includes a first answering circuit, a second answering controller, and a switch. By switching states of the switch, the first answering circuit and the second answering circuit can be alternatively and switchably connected to the antenna. The first answering circuit can send the first radio-frequency signal through the antenna with the energy obtained from the induced current generated by the antenna. The second answering circuit can send the second radio-frequency signal through the antenna with the energy obtained from the induced current generated by the antenna.

The operating member can switch the states of the switch by switching between the first position and the second position.

In still another exemplary implementation of the calling device of a magnetic resonance imaging system, the answering controller includes a first memory, a second memory, a signal generator, and a processor. The first memory is configured to store a first data. The second memory is configured to store a second data. The signal generator can generate the first radio-frequency signal according to the first data, and generate the second radio-frequency signal according to the second data. The signal generator can send the first radio-frequency signal and the second radio-frequency signal through the antenna. The processor is connected to the first memory, the second memory, and the signal generator. The processor is configured to, when the operating member is in the first position, send the first data to the signal generator to generate the first radio-frequency signal, and when the operating member is in the second position, send the second data to the signal generator to generate the second radio-frequency signal.

In yet another exemplary implementation of the calling device of a magnetic resonance imaging system, the main body has an accommodating cavity. The antenna and the answering controller are arranged in the accommodating cavity. The operating member penetrates the main body. The call maker further includes a return spring. The return spring can apply an elastic force to the operating member to move same to the first position. This structure is simple, and is convenient to operate.

In yet another exemplary implementation of the calling device of a magnetic resonance imaging system, the fixed-frequency electromagnetic wave, the first radio-frequency signal, and the second radio-frequency signal each have a frequency ranging from 800 MHz to 930 MHz. In this way, mutual interference between the calling device and a magnetic field of the magnetic resonance imaging system is avoided.

In still another exemplary implementation of the calling device of a magnetic resonance imaging system, the calling device further includes an alarm, where the alarm is connected to the reader/writer and can convert the prompt signals into acoustic signals or optical signals. This structure is simple, and has good stability.

In yet another exemplary implementation of the calling device of a magnetic resonance imaging system, the antenna is an omnidirectional antenna. In this way, an impact of a placement angle of the call maker on signals is avoided.

In still another exemplary implementation of the calling device of a magnetic resonance imaging system, the circuits in the answering controller are passive circuits. In this way, mutual interference between a battery and the magnetic field of the magnetic resonance imaging system is avoided.

The present disclosure further provides a magnetic resonance imaging system that includes a calling device as described above. The reader/writer can send a fixed-frequency electromagnetic wave to form a radio-frequency electromagnetic field in a detection area of the magnetic resonance imaging system. In the calling device of the magnetic resonance imaging system, an RFID technology is used to realize wireless interconnection between the reader/writer and the call maker, helping an operator to make a determination in time to stop an examination when the calling device has a fault, and in this way, high reliability is achieved.

Figure 1:
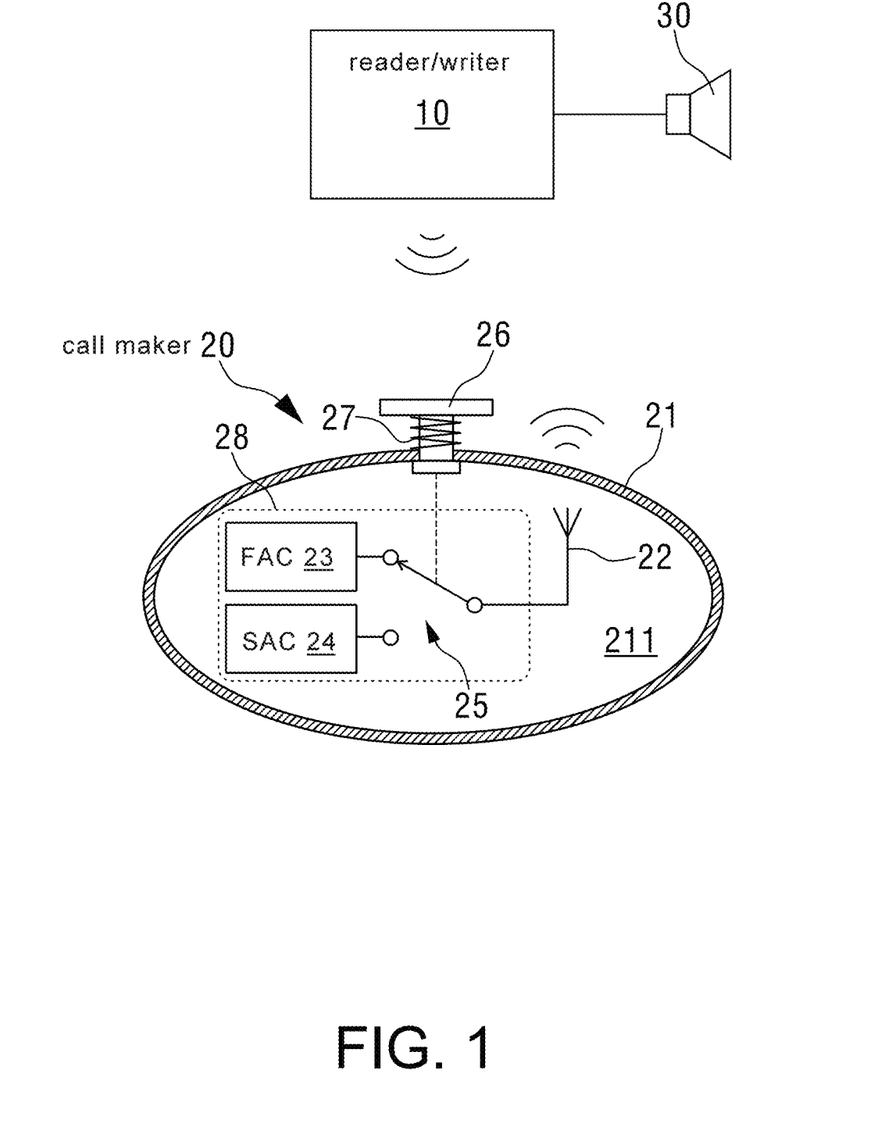
FIG. 1 is a calling device according to an exemplary embodiment of a magnetic resonance imaging system.
Figure 2:
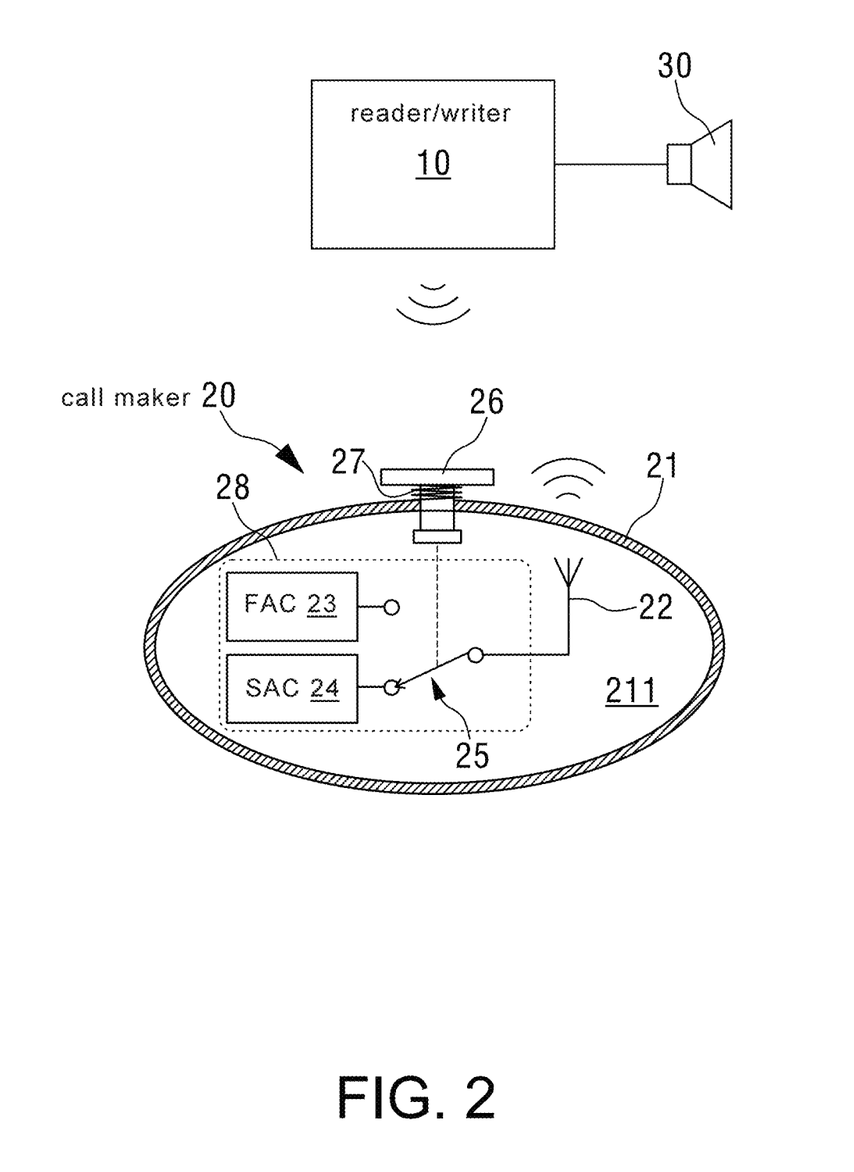
FIG. 2 shows the calling device of FIG. 1 in an alternate state according to an exemplary embodiment.

FIG. 1 is a schematic structural diagram of an exemplary implementation of a calling device of a magnetic resonance imaging system, and FIG. 2 is a schematic diagram showing change states of the calling device shown in FIG. 1. As shown in FIG. 1, the calling device of a magnetic resonance imaging system includes a reader/writer 10 and a call maker 20. The reader/writer 10 is configured to send a fixed-frequency electromagnetic wave to form a radio-frequency electromagnetic field in a detection area of the magnetic resonance imaging system.

As shown in FIG. 1, the call maker 20 includes a main body 21, an antenna 22, an operating member 26, and an answering controller 28. The antenna 22, the operating member (button) 26, and the answering controller 28 are arranged on the main body 21. As shown in FIG. 1, in this exemplary implementation, the main body 21 has an accommodating cavity 211. The antenna 22 and the answering controller 28 are arranged in the accommodating cavity 211 so that they are less prone to being damaged. However, it is not limited to this. The main body 21 is in the shape of an ellipsoid that is easy to hold by hand, but is not limited thereto. In an exemplary embodiment, the answering controller 28 includes processing circuitry that is configured to perform one or more functions and/or operations of the answering controller 28. Additionally or alternatively, one or more of the components of the answering controller 28 may include processing circuitry configured to perform one or more respective functions and/or operations of the component(s).

The antenna 22 is configured to generate an induced current after receiving the fixed-frequency electromagnetic wave that is sent by the reader/writer 10. The operating member 26 is configured to switch between a first position (a position shown in FIG. 1) and a second position (a position shown in FIG. 2) relative to the main body 21. In this exemplary implementation, the operating member 26, for example, a button, penetrates the main body 21. The answering controller 28 is connected to the antenna 22. The answering controller 28 is configured such that: when the operating member 26 is in the first position, the answering controller 28 is configured to send a first radio-frequency signal through the antenna 22 with energy obtained from the induced current generated by the antenna 22, and when the operating member 26 is in the second position, the answering controller 28 is configured to send a second radio-frequency signal through the antenna 22 with energy obtained from the induced current generated by the antenna 22.

Specifically, in this exemplary implementation, the answering controller 28 includes a first answering circuit 23, a second answering circuit 24, and a switch 25. By switching states of the switch 25, the first answering circuit 23 and the second answering circuit 24 are configured to be alternatively and switchably connected to the antenna 22. The switch 25 has, for example, a pair of normally closed contacts and a pair of normally open contacts. Specifically, when the switch 25 is in a state (i.e., the normally closed contacts are closed, and the normally open contacts are opened) shown in FIG. 1, the first answering circuit 23 is connected to the antenna 22. When the switch 25 is in a state (i.e., the normally open contacts are closed, and the normally closed contacts are opened) shown in FIG. 2, the second answering circuit 24 is connected to the antenna 22. The operating member 26 is configured to switch the states of the switch 25 by switching between the first position and the second position. The operating member 26 switches the states of the switch 25 by mechanical transmission, for example.

In this exemplary implementation, for ease of operation, the call maker 20 further includes a return spring 27. The return spring 27 is configured to apply an elastic force to the operating member 26 to move same to the first position. Specifically, when the operating member 26 is applied with no external force, the operating member 26 is in the first position shown in FIG. 1 under the action of the return spring 27, the normally closed contacts of the switch 25 are closed while the normally open contacts thereof are opened due to the absence of an external force, and thus the first answering circuit 23 is connected to the antenna 22 through the switch 25; and when the operating member 26 is pressed with an external force, the operating member 26 overcomes the elastic force of the return spring 27 to move to the second position shown in FIG. 2, the normally open contacts of the switch 25 are closed while the normally closed contacts thereof are opened under driving of the operating member 26, and thus the second answering circuit 24 is connected to the antenna 22 through the switch 25.

When the first answering circuit 23 is connected to the antenna 22 through the switch 25, the first answering circuit 23 is configured to send a first radio-frequency signal through the antenna 22 with energy obtained from the induced current generated by the antenna 22. Information contained in the first radio-frequency signal refers to, for example, information prestored in the first answering circuit 23. When the second answering circuit 24 is connected to the antenna 22 through the switch 25, the second answering circuit 24 is configured to send a second radio-frequency signal through the antenna 22 with energy obtained from the induced current generated by the antenna 22. Information contained in the second radio-frequency signal refers to, for example, information prestored in the second answering circuit 24. The reader/writer 10 is configured to receive the first radio-frequency signal and the second radio-frequency signal and is configured to send different prompt signals according to the first radio-frequency signal and the second radio-frequency signal respectively.

In this exemplary implementation, the calling device further includes an alarm 30, where the alarm 30 is connected to the reader/writer 10 and is configured to convert the prompt signals into acoustic signals or optical signals (acoustic signals are taken as an example in this exemplary implementation). It can be understood that if the prompt signals are different, the corresponding acoustic or optical signals are also different. However, it is not limited to this. In other exemplary implementations, for example, the reader/writer 10 may be connected to a control system of the magnetic resonance imaging system, and content corresponding to the prompt signals is displayed on a display connected to the control system to prompt an operator.

Figure 4:
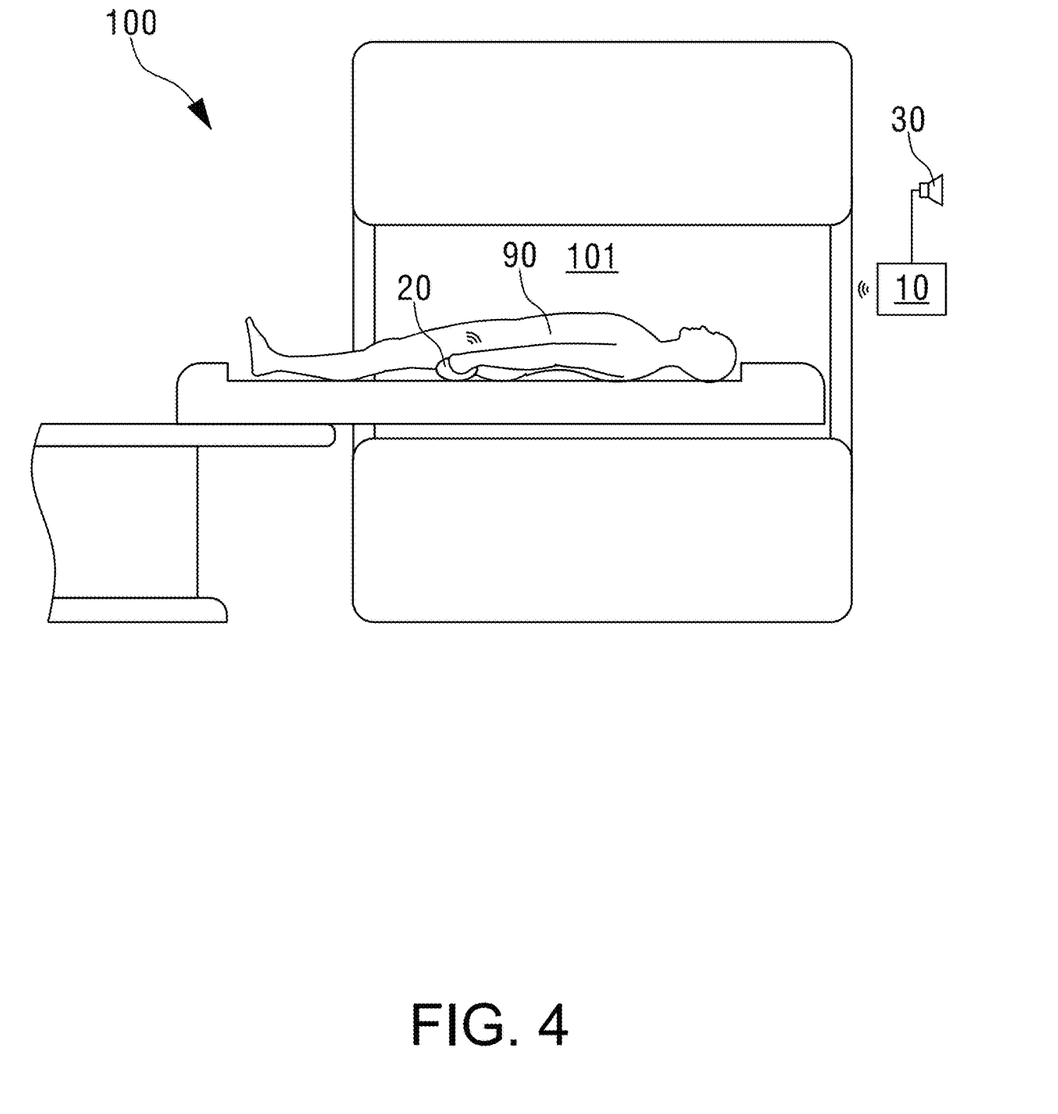
FIG. 4 is a magnetic resonance imaging system according to an exemplary embodiment.

FIG. 4 shows a state in which an examinee 90 is located in a detection area 101 of a magnetic resonance imaging system 100. An exemplary application scenario of the calling device is described below with reference to FIG. 4, which is not intended to limit the scope of protection of the present disclosure. When the calling device is in use, the reader/writer 10 forms a radio-frequency electromagnetic field in the detection area 101. The examinee 90 holding the call maker 20 is subjected to a magnetic resonance examination in the detection area 101, and in this case, the call maker 20 is in the radio-frequency electromagnetic field formed by the reader/writer 10. The call maker 20 is in the radio-frequency electromagnetic field, and thus the antenna 22 is configured to generate an induced current under the action of the fixed-frequency electromagnetic wave that is sent by the reader/writer 10.

When the examinee has no call demand, the examinee does not press the operating member 26, so the switch 25 is kept in the state shown in FIG. 1, the first answering circuit 23 is connected to the antenna 22 through the switch 25, and the first answering circuit 23 sends the first radio-frequency signal through the antenna 22 with the energy obtained from the induced current generated by the antenna 22. The reader/writer 10 receives the first radio-frequency signal and sends a prompt signal according to the first radio-frequency signal, and the alarm 30 converts the prompt signal into an acoustic signal, for example, beeps. The operator determines that the call maker 20 is in the radio-frequency electromagnetic field on the basis of the beeps (thereby inferring that the examinee is located in the detection area 101), the calling device can work normally, and the examinee does not call.

When the examinee has a call demand, the examinee presses the operating member 26, so the switch 25 is kept in the state shown in FIG. 2, the second answering circuit 24 is connected to the antenna 22 through the switch 25, and the second answering circuit 24 sends the second radio-frequency signal through the antenna 22 with the energy obtained from the induced current generated by the antenna 22. The reader/writer 10 receives the second radio-frequency signal and sends a prompt signal according to the second radio-frequency signal, and the alarm 30 converts the prompt signal into an acoustic signal, for example, bleeps. The operator determines that the call maker 20 is in the radio-frequency electromagnetic field on the basis of the bleeps (thereby inferring that the examinee is located in the detection area 101), the calling device can work normally, and the examinee is calling, so the operator stops the examination or contacts the examinee.

If the examinee holding the call maker 20 does not enter the detection area 101, the call maker 20 is out of the radio-frequency electromagnetic field formed by the reader/writer 10, no induced current is generated, the first answering circuit 23 and the second answering circuit 24 fail to send signals, and the alarm 30 makes no sound. When the calling device has a fault, the alarm 30 also makes no sound. The operator determines that the examinee does not enter the detection area 101 or the calling device has a fault, and then the operator stops the examination.

In the calling device in this exemplary implementation, an RFID (Radio Frequency Identification) technology is used to realize wireless interconnection between the reader/writer 10 and the call maker 20, helping the operator to make a determination in time to stop the examination when the calling device has a fault, and in this way, high reliability is achieved.

In the foregoing exemplary implementation, the calling device is only provided with one operating member 26 and one return spring 27, but is not limited to this. In other exemplary implementations, a plurality of operating members and a plurality of return springs may be correspondingly arranged as needed, so that the switch 25 is configured to be triggered from multiple angles.

In an exemplary implementation, the fixed-frequency electromagnetic wave that is sent by the reader/writer 10, the first radio-frequency signal, and the second radio-frequency signal each have a frequency ranging from 800 MHz to 930 MHz. In this way, mutual interference between the calling device and a magnetic field of the magnetic resonance imaging system is avoided. However, it is not limited to this. In other exemplary implementations, the foregoing frequency may be adjusted according to needs.

In an exemplary implementation, the antenna 22 is an omnidirectional antenna. In this way, an impact of a placement angle of the call maker 20 on signals is avoided.

In an exemplary implementation, the circuits in the answering controller 28 are passive circuits. In this way, mutual interference between a battery and the magnetic field of the magnetic resonance imaging system is avoided.

Figure 3:
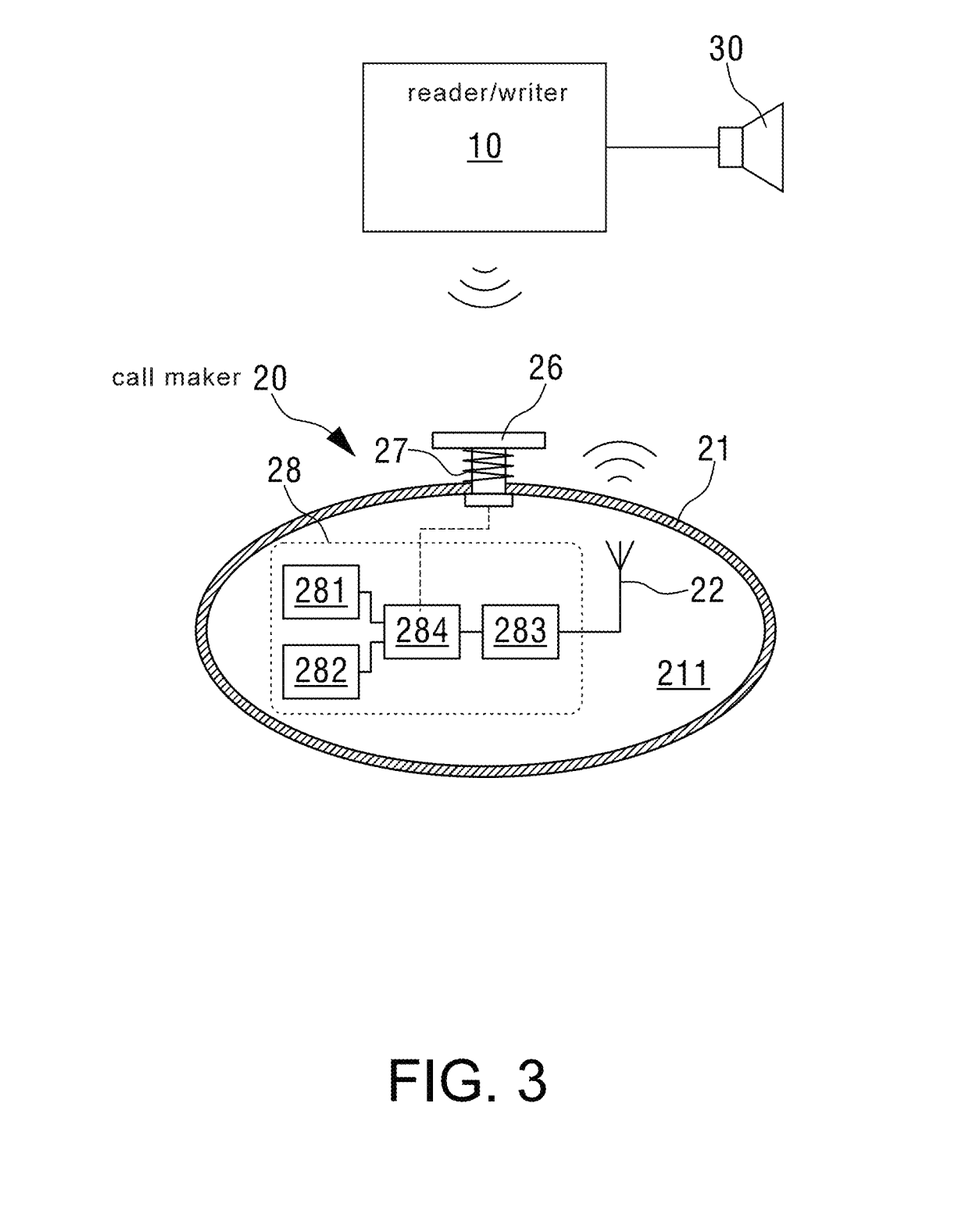
FIG. 3 is a calling device according to an exemplary embodiment of a magnetic resonance imaging system.

FIG. 3 is a schematic structural diagram of another exemplary implementation of the calling device of a magnetic resonance imaging system. The similarities between the calling device in this exemplary implementation and the calling device shown in FIG. 1 are not repeated here, and the difference between the two lies in the answering controller 28.

In this exemplary implementation, the answering controller 28 includes a first memory 281, a second memory 282, a signal generator 283, and a processor 284. The first memory 281 is configured to store a first data. The second memory 282 is configured to store a second data.

The processor 284 is connected to the first memory 281, the second memory 282, and the signal generator 283. The processor 284 is configured such that: when the operating member 26 is in the first position, the processor 284 sends the first data to the signal generator 283, and when the operating member 26 is in the second position, the processor 284 sends the second data to the signal generator 283. The processor 284 obtains position information of the operating member 26 through a position sensor, for example, but is not limited to this.

The signal generator 283 is configured to generate a first radio-frequency signal according to the first data, and generate a second radio-frequency signal according to the second data. The signal generator 283 is configured to send the first radio-frequency signal and the second radio-frequency signal through the antenna 22.

An exemplary application scenario of the calling device is described below with reference to FIG. 4, which is not intended to limit the scope of protection of the present disclosure. When the calling device is in use, the reader/writer 10 forms a radio-frequency electromagnetic field in the detection area 101. The examinee 90 holding the call maker 20 is subjected to a magnetic resonance examination in the detection area 101, and in this case, the call maker 20 is in the radio-frequency electromagnetic field formed by the reader/writer 10. The call maker 20 is in the radio-frequency electromagnetic field, and thus the antenna 22 is configured to generate an induced current under the action of the fixed-frequency electromagnetic wave that is sent by the reader/writer 10.

When the examinee has no call demand, the examinee does not press the operating member 26, the operating member 26 is in the first position, the processor 284 sends the first data to the signal generator 283, and the signal generator 283 generates the first radio-frequency signal according to the first data and sends the first radio-frequency through the antenna 22. The reader/writer 10 receives the first radio-frequency signal and sends a prompt signal according to the first radio-frequency signal, and the alarm 30 converts the prompt signal into an acoustic signal, for example, bleeps. The operator determines that the call maker 20 is in the radio-frequency electromagnetic field on the basis of the bleeps (thereby inferring that the examinee is located in the detection area 101), the calling device can work normally, and the examinee does not call.

When the examinee has a call demand, the examinee presses the operating member 26, the operating member 26 is in the second position, the processor 284 sends the second data to the signal generator 283, and the signal generator 283 generates the second radio-frequency signal according to the second data and sends the second-radio frequency signal through the antenna 22. The reader/writer 10 receives the second radio-frequency signal and sends a prompt signal according to the second radio-frequency signal, and the alarm 30 converts the prompt signal into an acoustic signal, for example, bleeps. The operator determines that the call maker 20 is in the radio-frequency electromagnetic field on the basis of the bleeps (thereby inferring that the examinee is located in the detection area 101), the calling device can work normally, and the examinee is calling, so the operator stops the examination or contacts the examinee.

If the examinee holding the call maker 20 does not enter the detection area 101, the call maker 20 is out of the radio-frequency electromagnetic field formed by the reader/writer 10, no induced current is generated, the answering controller 28 fails to send signals, and the alarm 30 makes no sound. When the calling device has a fault, the alarm 30 also makes no sound. The operator determines that the examinee does not enter the detection area 101 or the calling device has a fault, and then the operator stops the examination.

In the calling device in this exemplary implementation, an RFID (Radio Frequency Identification) technology is used to realize wireless interconnection between the reader/writer and the call maker, helping the operator to make a determination in time to stop the examination when the calling device has a fault, and in this way, high reliability is achieved.

The present disclosure further provides a magnetic resonance imaging system, and in an exemplary implementation, as shown in FIG. 4, the magnetic resonance imaging system includes a calling device shown in FIG. 1 or FIG. 3. The reader/writer 10 is configured to send a fixed-frequency electromagnetic wave to form a radio-frequency electromagnetic field in the detection area 101 of the magnetic resonance imaging system 100. In the calling device of the magnetic resonance imaging system, an RFID (Radio Frequency Identification) technology is used to realize wireless interconnection between the reader/writer and the call maker, helping the operator to make a determination in time to stop the examination when the calling device has a fault, and in this way, high reliability is achieved.

It should be understood that, although the specification is described according to various embodiments, not each of the embodiments only contains one independent technical solution.

This description of the specification is merely for the sake of clarity. Those skilled in the art should take the specification as a whole, and the technical solutions in the various embodiments may also be combined appropriately to form other implementations which can be understood by those skilled in the art.

The series of detailed descriptions set forth above are merely specific illustrations of feasible embodiments of the present disclosure, and are not intended to limit the protection scope of the present disclosure. Equivalent implementations or variations without departing from the technical spirit of the present disclosure, such as combinations, divisions, or repetitions of the features, should fall within the protection scope of the present disclosure.

To enable those skilled in the art to better understand the solution of the present disclosure, the technical solution in the embodiments of the present disclosure is described clearly and completely below in conjunction with the drawings in the embodiments of the present disclosure. Obviously, the embodiments described are only some, not all, of the embodiments of the present disclosure. All other embodiments obtained by those skilled in the art on the basis of the embodiments in the present disclosure without any creative effort should fall within the scope of protection of the present disclosure.

It should be noted that the terms "first", "second", etc. in the description, claims and abovementioned drawings of the present disclosure are used to distinguish between similar objects, but not necessarily used to describe a specific order or sequence. It should be understood that data used in this way can be interchanged as appropriate so that the embodiments of the present disclosure described here can be implemented in an order other than those shown or described here. In addition, the terms "comprise" and "have" and any variants thereof are intended to cover non-exclusive inclusion. For example, a process, method, system, product or equipment comprising a series of steps or modules or units is not necessarily limited to those steps or modules or units which are clearly listed, but may comprise other steps or modules or units which are not clearly listed or are intrinsic to such processes, methods, products or equipment.

References in the specification to "one embodiment," "an embodiment," "an exemplary embodiment," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

The exemplary embodiments described herein are provided for illustrative purposes, and are not limiting. Other exemplary embodiments are possible, and modifications may be made to the exemplary embodiments. Therefore, the specification is not meant to limit the disclosure. Rather, the scope of the disclosure is defined only in accordance with the following claims and their equivalents.

Embodiments may be implemented in hardware (e.g., circuits), firmware, software, or any combination thereof. Embodiments may also be implemented as instructions stored on a machine-readable medium, which may be read and executed by one or more processors. A machine-readable medium may include any mechanism for storing or transmitting information in a form readable by a machine (e.g., a computer). For example, a machine-readable medium may include read only memory (ROM); random access memory (RAM); magnetic disk storage media; optical storage media; flash memory devices; electrical, optical, acoustical or other forms of propagated signals (e.g., carrier waves, infrared signals, digital signals, etc.), and others. Further, firmware, software, routines, instructions may be described herein as performing certain actions. However, it should be appreciated that such descriptions are merely for convenience and that such actions in fact results from computing devices, processors, controllers, or other devices executing the firmware, software, routines, instructions, etc. Further, any of the implementation variations may be carried out by a general-purpose computer.

For the purposes of this discussion, the term "processing circuitry" shall be understood to be circuit(s) or processor(s), or a combination thereof. A circuit includes an analog circuit, a digital circuit, data processing circuit, other structural electronic hardware, or a combination thereof. A processor includes a microprocessor, a digital signal processor (DSP), central processor (CPU), application-specific instruction set processor (ASIP), graphics and/or image processor, multi-core processor, or other hardware processor. The processor may be "hard-coded" with instructions to perform corresponding function(s) according to aspects described herein. Alternatively, the processor may access an internal and/or external memory to retrieve instructions stored in the memory, which when executed by the processor, perform the corresponding function(s) associated with the processor, and/or one or more functions and/or operations related to the operation of a component having the processor included therein. In one or more of the exemplary embodiments described herein, the memory is any well-known volatile and/or non-volatile memory, including, for example, read-only memory (ROM), random access memory (RAM), flash memory, a magnetic storage media, an optical disc, erasable programmable read only memory (EPROM), and programmable read only memory (PROM).

The memory can be non-removable, removable, or a combination of both.

Reference List

10 Reader/writer
20 Call maker
21 Main body
211 Accommodating cavity
22 Antenna
23 First answering circuit
24 Second answering circuit
25 Switch
26 Operating member
27 Return spring
28 Answering controller
281 First storage (memory)
282 Second storage (memory)
283 Signal generator
284 Processor
30 Alarm
90 Examinee
100 Magnetic resonance imaging system
101 Detection area

The invention claimed is:

1. A calling device of a magnetic resonance imaging system, comprising:
 a reader/writer configured to send a fixed-frequency electromagnetic wave to form a radio-frequency (RF) electromagnetic field in a detection area of the magnetic resonance imaging system; and
 a call maker comprising:
  a main body,
  an antenna that is arranged on the main body and configured to generate an induced current after receiving the fixed-frequency electromagnetic wave,
  an operating member that is arranged on the main body and configured to switch between a first position and a second position relative to the main body, and
  an answering controller that is arranged on the main body and connected to the antenna, wherein the answering controlling includes a first answering circuit having a first RF Identification (RFID) and a second answering circuit having a second RFID including different identification information than the first RFID, the answering controller being configured to:
   in response to the operating member being in the first position, send a first radio-frequency signal through the antenna with energy obtained from the induced current generated by the antenna;

in response to the operating member being in the second position, send a second radio-frequency signal through the antenna with energy obtained from the induced current generated by the antenna, wherein the reader/writer is configured to receive the first radio-frequency signal and the second radio-frequency signal, and send different prompt signals according to the first radio-frequency signal and the second radio-frequency signal, respectively.

2. The calling device of claim 1, wherein the answering controller further comprises:
a switch configured to switch between switching states to alternatively and switchably connect the first answering circuit and the second answering circuit to the antenna, wherein:
the first answering circuit is configured to send the first radio-frequency signal through the antenna with the energy obtained from the induced current generated by the antenna;
the second answering circuit is configured to send the second radio-frequency signal through the antenna with the energy obtained from the induced current generated by the antenna; and
the operating member is configured to switch the states of the switch by switching between the first position and the second position.

3. The calling device of claim 1, wherein the answering controller further comprises:
a first memory that is configured to store a first data,
a second memory that is configured to store a second data,
a signal generator that is configured to:
generate the first radio-frequency signal according to the first data and generate the second radio-frequency signal according to the second data, and
send the first radio-frequency signal and the second radio-frequency signal through the antenna, and
a processor that is connected to the first memory, the second memory, and the signal generator, the processor being configured to:
in response to the operating member being in the first position, send the first data to the signal generator to generate the first radio-frequency signal, and
in response to the operating member being in the second position, send the second data to the signal generator to generate the second radio-frequency signal.

4. The calling device of claim 1, wherein:
the main body has an accommodating cavity, the antenna and the answering controller being arranged in the accommodating cavity;
the operating member is configured to penetrate the main body; and
the call maker further comprises a return spring that is configured to apply an elastic force to the operating member to move the operating member to the first position.

5. The calling device of claim 1, wherein the fixed-frequency electromagnetic wave, the first radio-frequency signal, and the second radio-frequency signal each have a frequency ranging from 800 MHz to 930 MHz.

6. The calling device of claim 1, wherein the calling device further comprises an alarm connected to the reader/writer and configured to convert the prompt signals into one or more acoustic signals or one or more optical signals.

7. The calling device of claim 1, wherein the antenna is an omnidirectional antenna.

8. The calling device of claim 1, wherein the answering controller includes one or more passive circuits.

9. A magnetic resonance imaging system, comprising the calling device of claim 1.

10. The magnetic resonance imaging system of claim 9, wherein the reader/writer is configured to send a fixed-frequency electromagnetic wave to form a radio-frequency electromagnetic field in a detection area of the magnetic resonance imaging system.

11. The calling device of claim 1, wherein the first answering circuit and the second answering circuit are passive circuits.

12. The calling device of claim 1, wherein the first answering circuit and the second answering circuit are powered by energy obtained from the induced current generated by the antenna.

13. The calling device of claim 1, wherein the calling device is free of a battery power source.

14. The calling device of claim 1, wherein the calling device is exclusively powered by energy obtained from the induced current generated by the antenna.

* * * * *